United States Patent [19]
Meagher et al.

[11] Patent Number: 5,981,237
[45] Date of Patent: Nov. 9, 1999

[54] METHOD FOR LIQUEFACTION OF CEREAL GRAIN STARCH SUBSTRATE AND APPARATUS THEREFOR

[75] Inventors: Michael M. Meagher; Daryl D. Grafelman, both of Lincoln, Nebr.

[73] Assignee: Board of Regents, Lincoln, Nebr.

[21] Appl. No.: 08/565,086

[22] Filed: Nov. 30, 1995

[51] Int. Cl.$^6$ .............................. C12P 19/14; C12P 7/06
[52] U.S. Cl. .............................. 435/99; 435/151; 435/161
[58] Field of Search ................................ 435/99, 161, 151

[56] References Cited

U.S. PATENT DOCUMENTS

5,059,439  10/1991  Wenger et al. ........................... 426/451

OTHER PUBLICATIONS

Author: Galen J. Rokey, Title: Extrusion Cooking of Cereal Grain as an Initial Process in the Production of Ethanol Date: Aug. 21, 1990, pp. 529–542, Pub. Wenger Manufacturing, Inc.

Author: Daryl D. Grafelman, Michael M. Meagher, Title: Liquefaction of Starch By a Single–screw Extruder and Post–Extrusion Static–mixer Reactor, Date: Feb. 18, 1994, pp. 529–542, Pub. Nebraska Agricultural Experiment Station, Lincoln, NE.

Davidson, V.J. et al. 1984. J. Food Science 49: 453–458.

Weu, L.F. et al. 1990. Cereal Chemistry 67(3): 268–275.

Lee, Y.C. et al. J. Food Science 55(5): 1365–1366, 1372.

Lammers, G. et al. 1994. Chemical Eng. Res. & Design 72(A5): 728–732.

Tsayev, A.I et al. 1992. Polymer Eng. & Sci. 32(2): 85–93.

Lammers J. et al. 1993. Starch 45(7): 227–232.

*Primary Examiner*—Toni R. Scheiner
*Attorney, Agent, or Firm*—Suiter & Associates PC

[57] ABSTRACT

A method and apparatus are disclosed for liquefaction of starch derived from cereal grain. A single-screw extruder is utilized to gelatinize a starch substrate providing significant advantage over prior art jet steam cookers. Liquefaction of the gelatinized starch substrate is completed by post-extrusion bioreaction of the starch with a static-mixer reactor. An alpha-amylase enzyme is utilized to facilitate the liquefaction process. The Liquefacted starch substrate is heated after bioreaction to achieve complete digestion of remaining starch inclusions. Liquefacted starch substrates utilizing the disclosed process significantly reduce the amount of energy required in the conversion of starch to fermentable sugars in the production of ethanol.

28 Claims, 6 Drawing Sheets

1

METHOD FOR LIQUEFACTION OF CEREAL GRAIN STARCH SUBSTRATE AND APPARATUS THEREFOR

TECHNICAL FIELD

The present invention relates generally to liquefaction of cereal grain starch substrates and specifically to liquefaction of cereal grain starches with a single-screw extruder and post-extrusion reactor.

BACKGROUND OF THE INVENTION

Liquefaction of starch derived from cereal grains is utilized in the production of a variety of grain derived products. Grain-derived products include common food products such as breakfast cereals, pet foods and livestock feed, for example. Liquefaction of grain-derived starches is also used in the production of ethanol which is utilized in the production of combustible fuels the most common of which is gasohol, a 10% blend of grain derived ethanol with petroleum derived gasoline.

The production of ethanol in the United States has dramatically increased in recent years. The mandated use of oxygenates such as ethanol in gasoline by the Environmental Protection Agency's Renewable Oxygenate Requirement will result in further increases in the production of ethanol in the near future.

In order to produce ethanol from a cereal grain substrate, the grain substrate must be gelatinized, liquefied and saccharified before being fermented into ethanol which often includes enzymatic hydrolysis. The conversion of cereal grain starch into fermentable sugars consumes 30% of the total energy required for alcohol fermentation and is one of the major problems encountered the ethanol production industry.

Methods for converting a grain substrate into a liquefied starch solution are known in the art. The most commonly utilized method for starch liquefaction is jet steam cooking. However, jet steam cooking requires the grain substrate slurry, which is to be cooked, first have a minimum moisture content of 60–70% m.c.w.b. Because jet steam cooking requires such a high moisture content, the jet steam cooking process consumes a considerable amount of energy to heat the water contained in the starch slurry solution. However, reducing the moisture content of the starch solution in a jet steam cooker results in an output product that is difficult to pump and process due to very high viscosities. Further processing with enzymes is also very difficult at lower moisture contents using a jet cooker. Thus, there lies a need for a low energy consuming method of grain liquefaction the grain solution is processed with low moisture contents that results in a product suitable for enzymatic hydrolysis.

SUMMARY OF THE INVENTION

The present invention provides liquefaction of starch derived from cereal grain by utilization of a single-screw extruder followed by post-extrusion bioreaction of the starch with a static-mixer reactor. The present invention provides a cost-effective means for gelatinization and liquefaction of grain starches by processing the starch substrate at lower moisture content levels measured by weight than with prior methods. The lower moisture content levels of the starch substrate translate into less energy consumed in the heating of the moisture contained therein resulting in less energy consumed in the overall liquefaction process. The processing parameters herein described may also be employed with other extruders such as twin-screw extruders.

BRIEF DESCRIPTION OF THE DRAWINGS

The numerous objects and advantages of the present invention may be better understood by those skilled in the art by reference to the accompanying figures in which.

DETAILED DESCRIPTION OF AN EXEMPLARY EMBODIMENT

Figure 1:
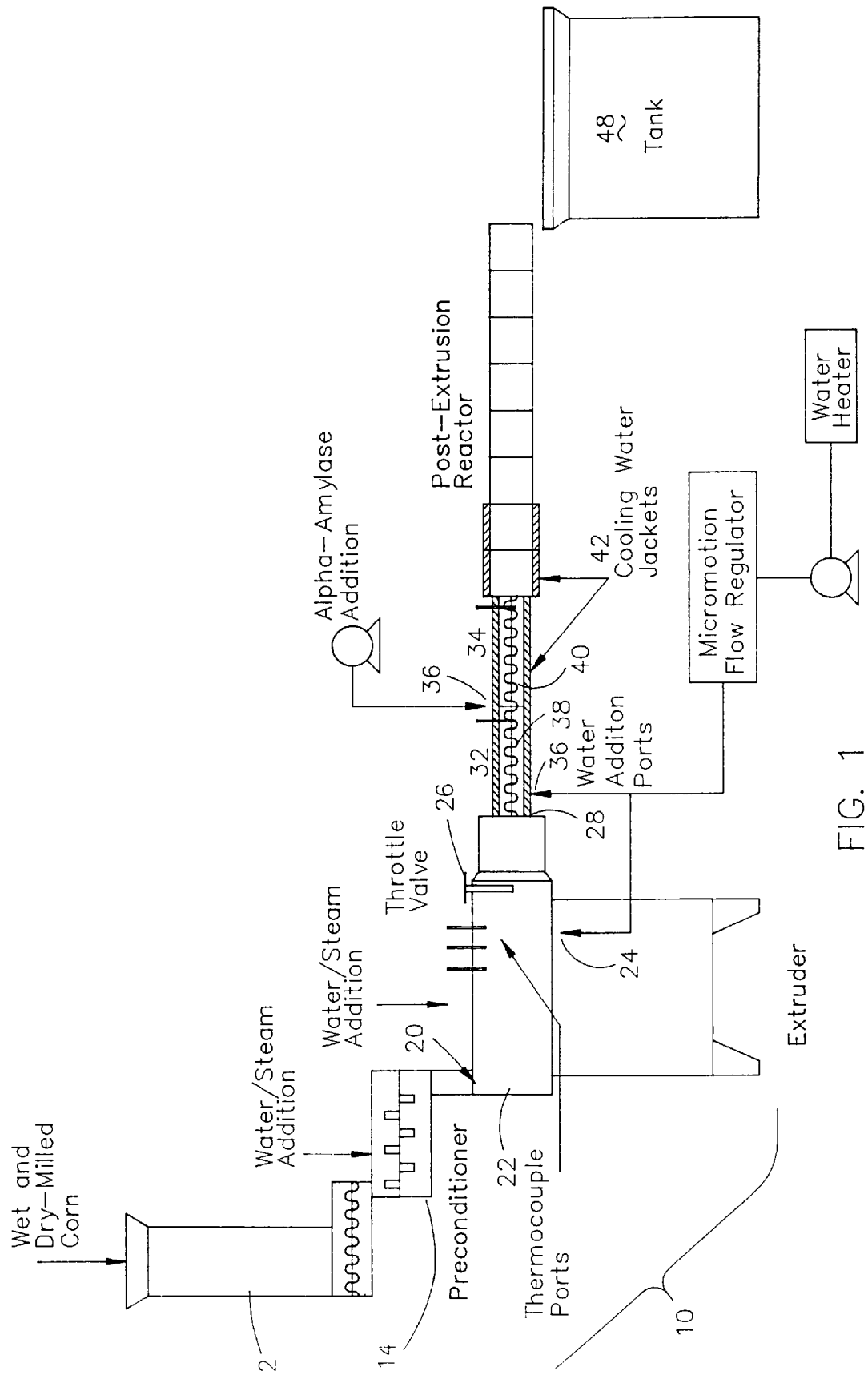
FIG. 1 is a diagram of the present invention illustrating somewhat schematically apparatus for wet- and dry-milled corn extrusion.

FIG. 1 is a schematic illustration of the present invention in which an extruder is utilized as a starch gelatinizer in lieu of a jet stream cooker for gelatinization and cooking of a starch substrate. In an exemplary embodiment of the present invention, the extruder bioreactor system 10 preferably includes a single-screw extruder 22. The single-screw extruder 22 is preferred over twin-screw extruders because of the greater capital and operational costs associated with twin-screw extruders as compared with single-screw extruders. The purpose of utilizing a single-screw extruder is to reduce the energy consumption and ultimately the costs of gelatinization and liquefaction of cereal grain starch.

LIQUEFACTION OF LOW MOISTURE WET-MILLED CORN

The extruder bioreactor system 10 as shown in FIG. 1 is configured to achieve optimal results in the processing of a cereal grain substrate which is preferably wet-milled corn having a relatively low moisture content, approximately 10% m.c.w.b. Low moisture content starch substrate may be defined as having less than 30% m.c.w.b. The low moisture content grain substrate ("Wet and Dry-Milled Corn") is fed into a live feed bin 12 which adds the grain substrate into a preconditioning chamber ("Preconditioner") 14. In an exemplary embodiment of the present invention, the substrate raw material preferably feeds into the extruder 22 at a flow rate of 90–125 kg per hour, preferably at a rate of 122 kg per hour.

The preconditioner 14 preferably comprises a rotating cylinder including axially rotating mixing paddles concentrically disposed therein. The preconditioner cylinder 14 preferably rotates at 300 rpm. The preconditioner 14 is utilized to add and blend moisture to the low moisture starch substrate to attain a minimum moisture content level suitable for extrusion. Moisture in the form of water or steam ("Water/Steam Addition") of a preferred temperature of 60° C. for water or 150° C. for steam may be added to the preconditioner 14 at a preferred rate of 35 to 50 kg per hour and blended with the starch substrate material to thoroughly wet and provide the substrate with a moisture content ranging from 20.7% to 44.8% m.c.w.b. In a preferred embodiment of the present invention moisture is added to the starch substrate in the preconditioner 14 to provide substrate moisture content levels of 40% m.c.w.b.

The substrate output of the preconditioner 14 preferably feeds into the input feed port 20 of the single-screw extruder 22. The screw of the single-screw extruder preferably rotates at 425–540 rpm and alternatively may rotate at 150–600 rpm. The substrate raw material preferably feeds into the extruder 22 at a flow rate of 90–125 kg per hour, and additional water or steam ("Water/Steam Addition") may be added into the extruder at a preferred rate of 20 to 40 kg per hour and a preferred temperature of 60° C. for water or 150° C. for steam thereby providing the starch substrate material in the extruder 22 with a moisture content of 35 to 40% m.c.w.b. In a preferred embodiment of the present invention, moisture is added to the starch substrate in the extruder 22 to provide substrate moisture levels of 46% m.c.w.b. Additional water at a preferred temperature of 60° C. may be added to the extrudate at the post-extrusion point 28. Under the presently described conditions the extruder bioreactor system 10 preferably yields a fully gelatinized homogeneous extrudate having cook levels of 92% to 100% cooking.

Liquefaction of the extrudate is preferably performed by post-extrusion bioreaction. Extrudate is preferably fed into first and second post-extrusion static-mixer reactors 32 and 34 whereby a throttle valve 26 in the extruder 22 provides control over pressure and residence time. Each first and second static-mixer reactor dies 32 and 34 preferably comprises a 1.22 m length by 38 mm diameter section containing mixing inserts 38 and 40 each having 24 180° turns. The static-mixer reactors 32 and 34 are preferably fitted with eight slidably positional circumferential cooling jackets ("Cooling Water Jackets") 42 which may receive steam or cooling water for respectively heating or cooling the extrudate. Extrudate is preferably cooled with a first static-mixer reactor 32 to a temperature of approximately 100° C. and may be cooled to a temperature ranging from 95° to 105° C. Alpha-amylase enzyme ("Alpha-Amylase Addition") at a preferred temperature of 25° C. is preferably added to the extrudate material as the extrudate enters the second static-mixer reactor 34. In a preferred embodiment of the present invention alpha-amylase having an activity of 4300 units per milliliter is added to the extrudate at a preferred concentration of 0.6% volume per weight of dry starch and may vary in concentration from 0.1% to 2.0% volume per weight of dry starch. A 5 mM concentration of $CaCl_2$ is preferably added to the alpha-amylase to improve the stability and activity thereof. Additional water at a preferred temperature of 60° C. may be added to the extrudate material post extrusion, monitored and regulated with a flow regulator ("Micromotion Flow Regulator") at points 24 and 36. Water may be heated with any typical water heating apparatus ("Water Heater"). The extrudate is preferably pumped into a receiving tank ("Tank") 48 after liquefaction of the extrudate wherein the extrudate is preferably heated to 90° C. for a period of 15 minutes.

LIQUEFACTION OF LOW MOISTURE DRY-MILLED CORN

FIG.1 also shows a preferred embodiment of the present invention wherein low moisture content dry-milled corn having a moisture content of 10% m.c.w.b. may be liquefied by extrusion. The liquefaction process of dry-milled corn is essentially similar to the liquefaction of wet-milled corn. The dry-milled corn substrate is preferably fed into live feed bin 12 to achieve extruder feed rates of 139 kg per hour and may vary over a range of 95 to 215 kg per hour. The rotational speed of the screw of the extruder is preferably held at a constant rate of 540 rpm. Cold water ranging from 15° to 20° C. is preferably pumped into the preconditioner 14 at a rate ranging from 46 to 61 kg per hour and is preferably pumped at 50 kg per hour at a temperature of 15° C. Warm water ranging from 65° to 70° C. is preferably pumped into the extruder 22 at a rate ranging from 30 to 70 kg per hour and is preferably pumped at 50 kg per hour at 65° C. The total moisture content of the starch substrate during extrusion may range from 43% to 50% m.c.w.b. and is maintained at 45% m.c.w.b. in a preferred embodiment of the present invention. The percentage of cook of the extrusion process is preferably 97% to 100% cook. The addition of steam is not required to obtain gelatinization of dry-milled corn.

Liquefaction of the dry-milled corn is preferably performed by the addition of 0.5% volume per weight of dry starch concentration of alpha-amylase in the second static-mixer reactor 34. Water is preferably added to the extrudate to achieve a moisture content of 63% m.c.w.b. The extrudate is preferably pumped into receiving tank 48 and heated to 90° C for a duration of 15 minutes.

Figure 2:
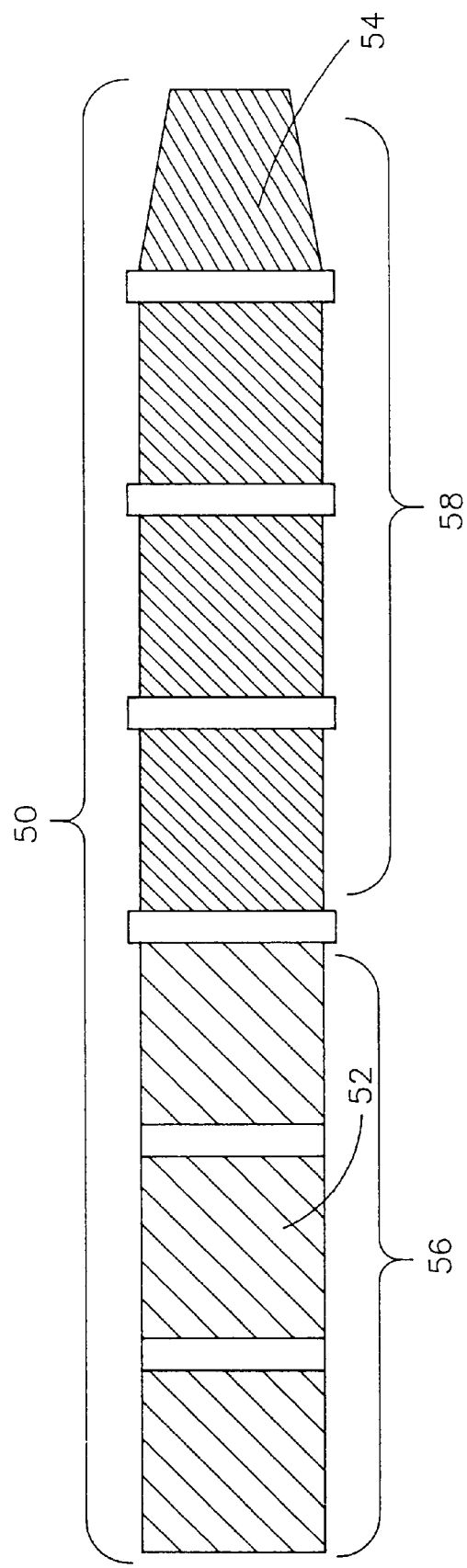
FIG. 2 is an illustration of the flight configuration of the screw utilized in the single-screw extruder depicted in FIG. 1.

FIG. 2 depicts the preferred configuration of the screw utilized in the extruder 22 of FIG. 1. The screw 50 preferably comprises a series of three concentric low shear cylindrical screw locks 56 followed by four concentric high shear cylindrical screw locks 58. The low shear screw locks 56 preferably comprise single flighted screw lock segments 52, and the high shear screw locks 58 preferably comprise double flighted screw lock segments 54. All of the flights of the screw 50 are preferably aligned in the same direction.

LIQUEFACTION OF HIGH MOISTURE WET-MILLED CORN STARCH SLURRY

Figure 3:
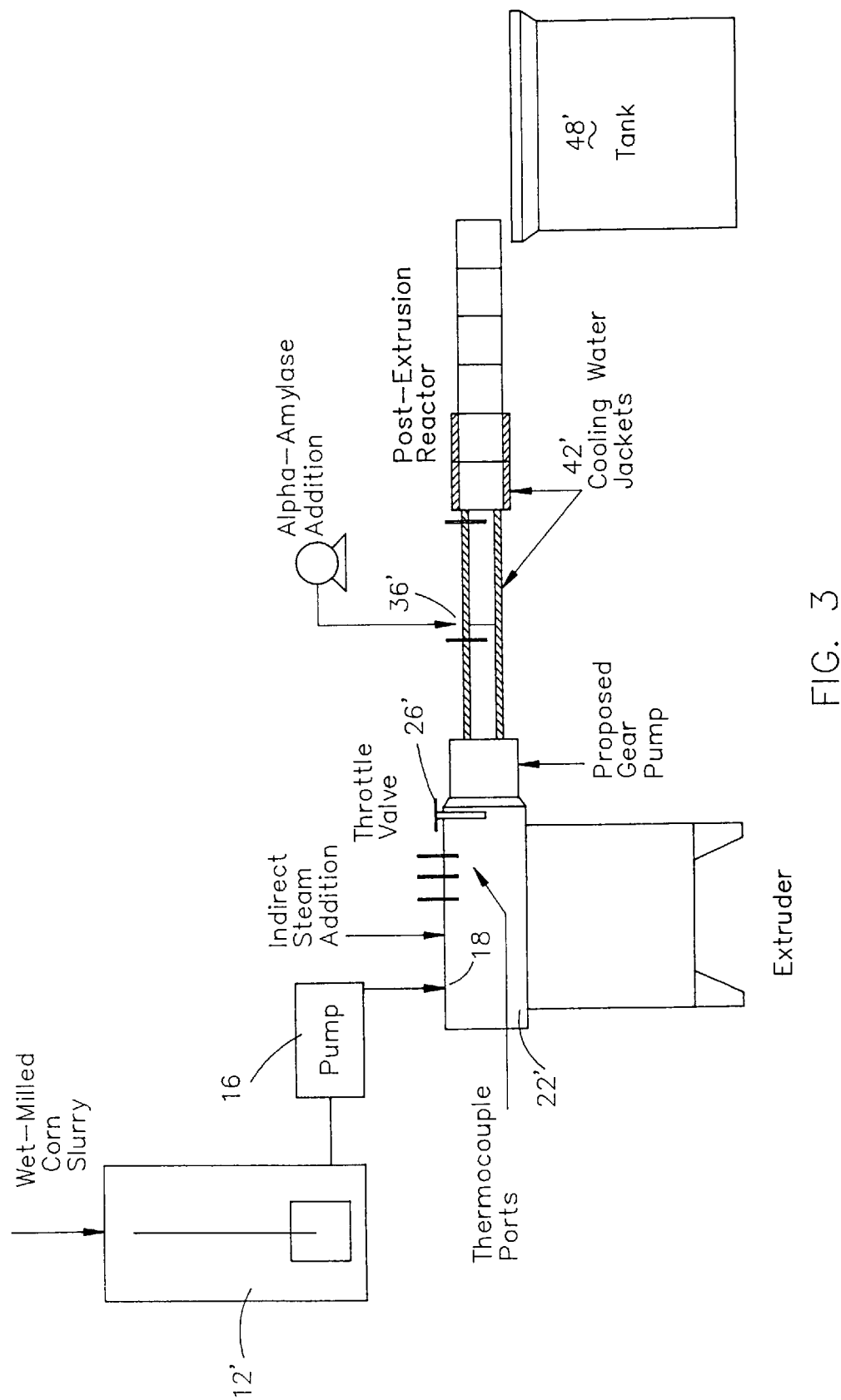
FIG. 3 is a diagram of the present invention illustrating somewhat schematically apparatus for wet-milled corn slurry extrusion.

FIG. 3 depicts a preferred configuration of the present invention for liquefaction of wet-milled corn starch slurry. A high moisture corn starch slurry ("Wet-Milled Corn Starch Slurry") may be inserted into feed bin 12 and is preferably pumped directly into extruder ("Extruder") 22' through inlet port 18 with a pump ("Pump") 16. Extrusion may gelatinize high moisture starch slurry having moisture contents up to 60% m.c.w.b. The high moisture starch slurry preferably has a moisture content of 58.5% m.c.w.b. The extrudate may be heated by the indirect steam addition ("Indirect Steam Addition") at the final three extrusion heads via corresponding thermocouple ports ("Thermocouple Ports").

Throttle valve ("Throttle Valve") 26' preferably regulates the extrudate output flow rate. To minimize backflow and leakage of the slurry in the extruder 22', the slurry is preferably pumped into extruder 22' at inlet port 18 corresponding to the third head of extruder 22'. Reduced throughput of the higher moisture content extrudate is preferably increased by utilization of a gear pump ("Proposed Gear Pump") directly before the post-extrusion reactor ("Post-Extrusion Reactor") to facilitate the flow of extrudate material thereinto. The high moisture slurry is preferably fed through the extruder 22' at a rate of 70 kg per hour. Alpha-amylase ("Alpha-Amylase Addition") having a preferred concentration of 1.3% volume per weight of starch is preferably added to the extrudate at inlet port 36' of the post-extrusion reactor. Cooling water jackets 42' essential similar to cooling jackets 42 of FIG. 1 are preferably utilized. The extrudate is preferably pumped into a receiving tank 48' and heated to 90° C. for a period of 15 minutes.

Figure 4:
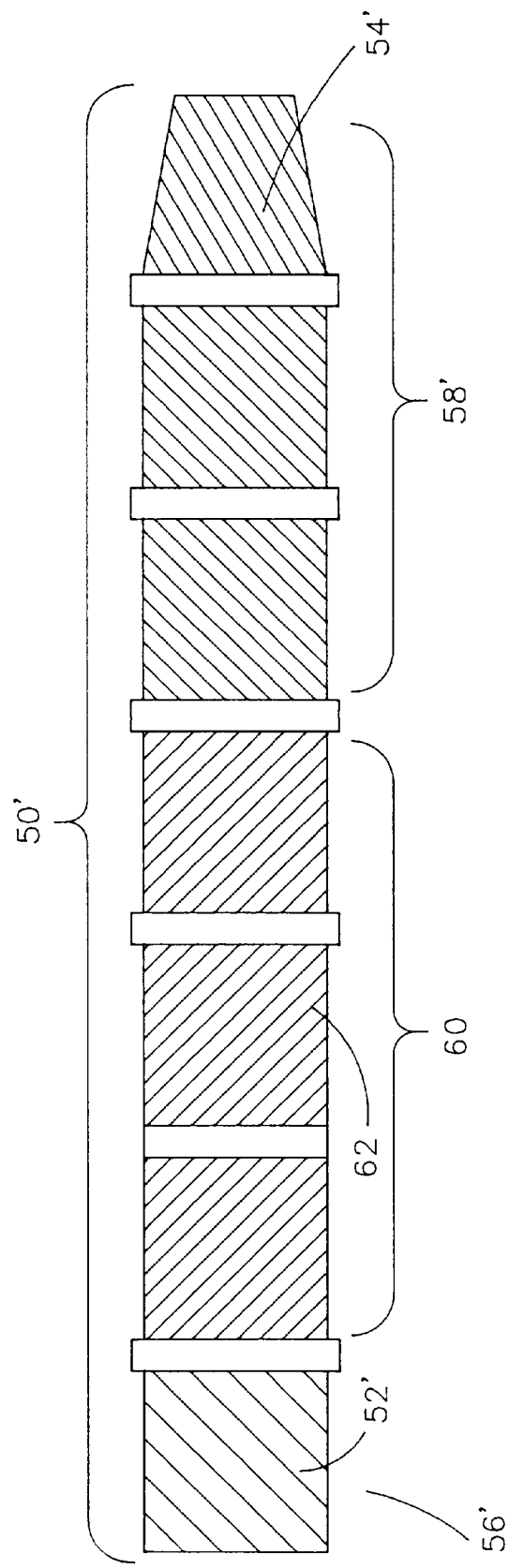
FIG. 4 is an illustration of the flight configuration of the screw utilized in the single-screw extruder depicted in FIG. 3.

FIG. 4 depicts the preferred configuration of the screw utilized in the extruder 22 of FIG. 3. The screw 50' preferably comprises a first low shear cylindrical screw lock 56' followed by a first series of three concentric higher shear cylindrical screw locks 60 followed by a second series of three yet higher shear concentric cylindrical screw locks 58'. The first low shear screw lock 56' preferably comprises a single flighted screw lock segment 52' aligned in a first direction, the first series of screw locks 60 preferably comprise reverse direction double flighted screw lock segments 62 aligned in a second direction and the second series of shear locks 58' preferably comprise double flighted screw lock segments 54' aligned in the first direction.

SCALABILITY OF VOLUMES

The foregoing volumes are operable in an extruder of equivalent size to the Wenger® X-20 extruder Scale-up to larger extrusion systems may be accomplished using the following scale-up factors:

| Wenger ® Extrusion System | Volume Scale-up Factor |
|---|---|
| X-20 | 1.00 |
| X-85 | 1.27 |
| X-165 | 9.27 |
| X-185 | 20.83 |
| X-235 | 26.92 |
| X-285 | 45.52 |

LIQUEFACTION OF STARCH UTILIZING PRIOR ART JET STEAM COOKING

Figure 5:
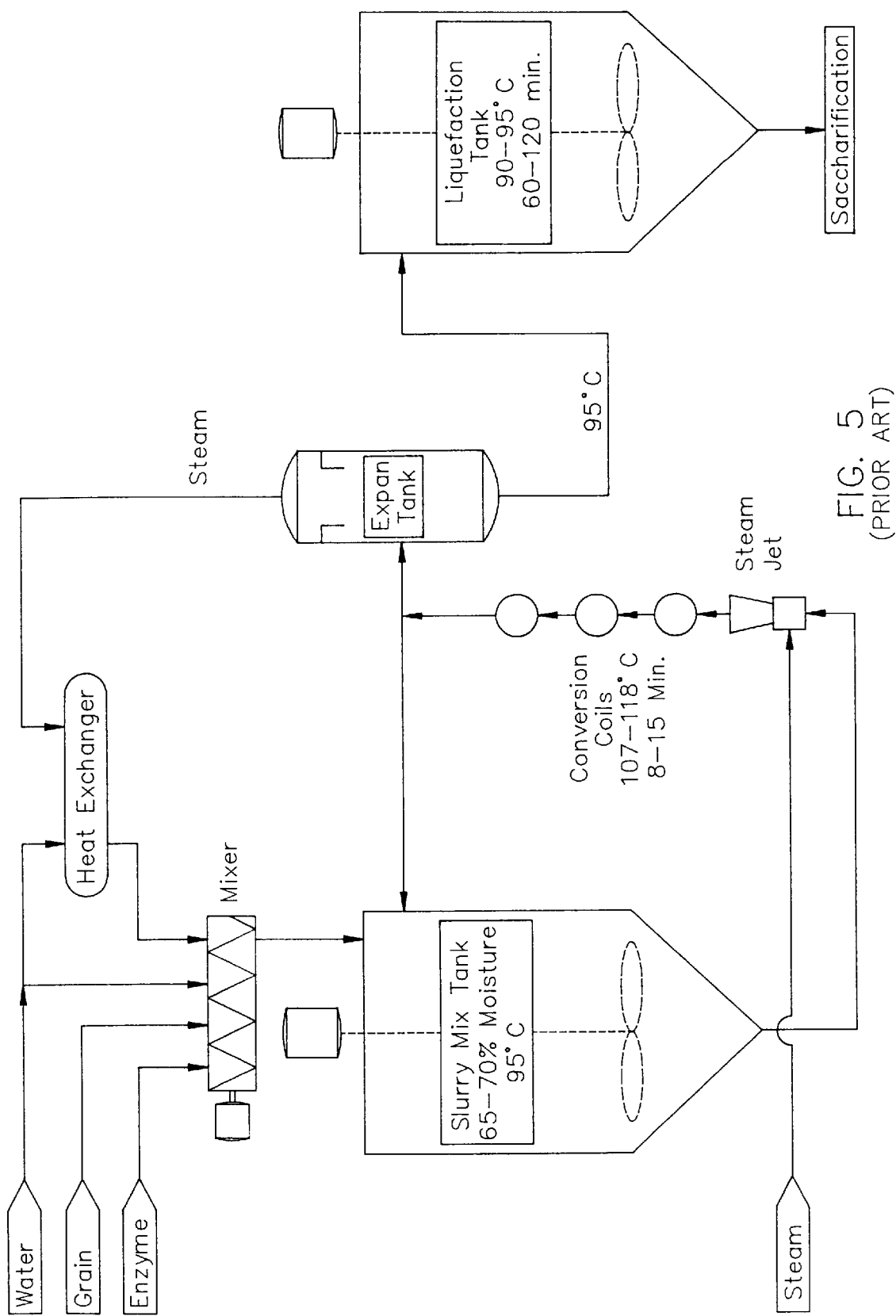
FIG. 5 is an illustration of a typical prior art jet steam cooker in the liquefaction of cereal grain starch.

FIG. 5 depicts a typical process flow configuration for liquefaction of starch such as utilized in the production of ethanol. Wet- and dry-milled corn are primarily used as starch substrates. The prior art jet steam cooking process is less efficient and consumes more energy than the process of the present invention primarily due the required high moisture content of the slurry which must contain a minimum of 65% to 70% m.c.w.b. compared with the minimum extrusion cooking moisture requirement of 30% m.c.w.b. Energy is consumed from the heating of the larger amounts of water present in the jet steam cooking process. Even high moisture content starch slurry may be extruded with moisture contents of only 58% m.c.w.b.

Figure 6A:
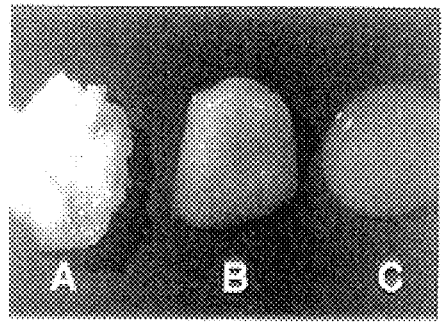
FIG. 6A, 6B and 6C illustrate the liquefaction progression of starch substrate in utilization of the present invention.
Figure 6B:
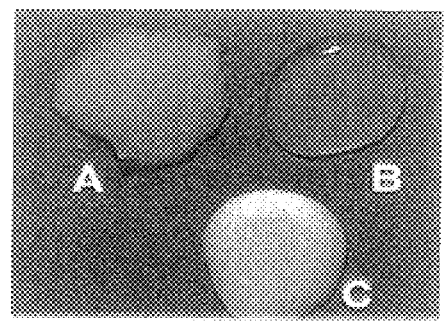
Figure 6C:
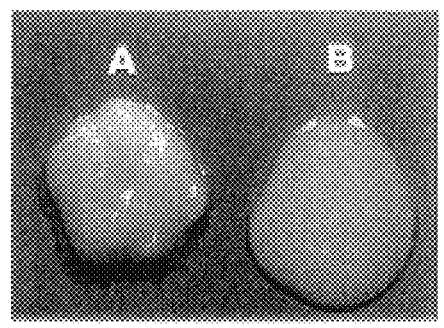

FIG. 6A, 6B and 6C illustrate the resulting progression of the liquefaction of starch in the process of the present invention. FIG. 6A depicts wet-milled corn A, extruded wet-milled corn B and liquefied wet-milled corn C respectively. FIG. 6B depicts wet-milled corn slurry A, extruded wet-milled corn slurry C and liquefied wet-milled corn slurry B. FIG. 6C depicts extruded dry-milled corn A and liquefied dry-milled corn B.

In view of the above detailed description of a preferred embodiment and modifications thereof, various other modifications will now become apparent to those skilled in the art. The claims below encompass the disclosed embodiments and all reasonable modifications and variations without departing from the spirit and scope of the invention.

What is claimed is:

1. A method for converting starch derived from a cereal grain starch substrate into a liquid utilizing a single-screw extruder, said method comprising:
   (a) preconditioning the cereal grain starch substrate in a preconditioning cylinder wherein moisture is blended with the starch substrate until the starch substrate reaches a first moisture content level;
   (b) varying the flow rate of the starch substrate through the single-screw extruder;
   (c) gelatinizing the preconditioned substrate with the single-screw extruder;
   (d) moisturizing the starch substrate during the extrusion thereof until the starch substrate reaches a second moisture content level;
   (e) heating the starch substrate during the extrusion thereof such that said gelatinization step is facilitated; and
   (f) bioreacting the gelatinized starch substrate with a static-mixer reactor, said bioreacting step including the addition of an alpha-amylase enzyme to the starch substrate; and
   (g) thereafter heating the starch substrate at a predetermined temperature for a predetermined duration such that remaining inclusions in the starch substrate may be sufficiently digested.

2. The method according to claim 1 wherein said preconditioning step includes increasing moisture content of the starch substrate from 20 percent to 45 percent moisture content on a weight basis.

3. The method according to claim 1 wherein said preconditioning step includes increasing moisture content of the starch substrate from 25 percent to 40 percent moisture content on a weight basis.

4. The method according to claim 1 wherein said preconditioning step includes increasing moisture content of the starch substrate from 30 percent to 35 percent moisture content on a weight basis.

5. The method according to claim 1 wherein said preconditioning step includes increasing moisture content of the starch substrate to 40 percent moisture content on a weight basis.

6. The method according to claim 1 wherein said preconditioning step includes adding moisture to the starch substrate at a rate from 35 kilograms to 50 kilograms per hour.

7. The method according to claim 1 wherein said preconditioning step includes adding moisture to the starch substrate at a rate from 40 kilograms to 45 kilograms per hour.

8. The method according to claim 1 wherein said preconditioning step includes rotating the cylinder at a rate ranging from 250 revolutions per minute to 350 revolutions per minute.

9. The method according to claim 1 wherein said varying step includes varying the flow rate of the starch substrate from 90 kilograms per hour to 125 kilograms per hour.

10. The method according to claim 1 wherein said varying step includes varying the flow rate of the starch substrate from 95 kilograms per hour to 120 kilograms per hour.

11. The method according to claim 1 wherein said varying step includes varying the flow rate of the starch substrate from 100 kilograms per hour to 115 kilograms per hour.

12. The method according to claim 1 wherein said varying step includes varying the flow rate of the starch substrate from 105 kilograms per hour to 110 kilograms per hour.

13. The method according to claim 1 wherein said varying step includes varying the flow rate of the starch substrate to 122 kilograms per hour.

14. The method according to claim 1 wherein said gelatinizing step includes rotating the screw of the extruder from 150 revolutions per minute to 600 revolutions per minute.

15. The method according to claim 1 wherein said gelatinizing step includes rotating the screw of the extruder from 425 revolutions per minute to 540 revolutions per minute.

16. The method according to claim 1 wherein said gelatinizing step includes rotating the screw of the extruder from 450 revolutions per minute to 525 revolutions per minute.

17. The method according to claim 1 wherein said gelatinizing step includes rotating the screw of the extruder from 475 revolutions per minute to 500 revolutions per minute.

18. The method according to claim 1 wherein said moisturizing step includes increasing moisture content of the starch substrate from 28 percent to 50 percent moisture content on a weight basis.

19. The method according to claim 1 wherein said moisturizing step includes increasing moisture content of the starch substrate from 35 percent to 45 percent moisture content on a weight basis.

20. The method according to claim 1 wherein said moisturizing step includes increasing moisture content of the starch substrate to 46 percent moisture content on a weight basis.

21. The method according to claim 1 wherein said moisturizing step includes adding moisture to the starch substrate at a rate from 20 kilograms per hour to 40 kilograms per hour.

22. The method according to claim 1 wherein said moisturizing step includes adding moisture to the starch substrate at a rate from 25 kilograms per hour to 35 kilograms per hour.

23. The method according to claim 1 wherein said preconditioning step includes adding moisture to the starch substrate at a temperature from 60° Celsius to 70° Celsius.

24. The method according to claim 1 wherein said moisturizing step includes adding moisture to the starch substrate at a temperature from 60° Celsius to 70° Celsius.

25. The method according to claim 1 wherein the extruder is a twin-screw extruder.

26. Liquefacted starch prepared according to a method for converting starch derived from a cereal grain starch substrate into a liquid, said method comprising:
  (a) preconditioning the cereal grain starch substrate in a preconditioning cylinder wherein moisture is blended with the starch substrate until the moisture content level of the starch substrate reaches a first level of 20 percent to 45 percent moisture content on a weight basis;
  (b) varying the flow rate of the preconditioned starch substrate through a single-screw extruder;
  (c) gelatinizing the preconditioned starch substrate with the single-screw extruder;
  (d) moisturizing the starch substrate during the extrusion thereof until the moisture content level of the starch substrate reaches a second level of 28 percent to 50 percent moisture content on a weight basis;
  (e) heating the starch substrate during the extrusion thereof such that said gelatinization step is facilitated; and
  (f) bioreacting the gelatinized starch substrate with a static-mixer reactor, said bioreacting step including the addition of an alpha-amylase enzyme to the starch substrate; and
  (g) thereafter heating the starch substrate at a predetermined temperature for a predetermined duration such that remaining inclusions in the starch substrate may be sufficiently digested.

27. A starch liquefaction system for converting starch derived from a cereal grain starch substrate into a liquid utilizing an extruder, said liquefaction system comprising:
  (a) a preconditioner comprising a preconditioning cylinder wherein moisture is blended with the starch substrate for providing the starch substrate with a first moisture content level;
  (b) an extruder having a single screw, said extruder operatively connected to said preconditioner for receiving and gelatinizing the starch substrate;
  (b) means for varying the flow rate of the starch substrate through said extruder;
  (d) means for moisturizing the starch substrate processed by said extruder such that the starch substrate reaches a second moisture content level;
  (e) means for heating the starch substrate processed by said extruder such that the gelatinization thereof is facilitated; and
  (f) a static-mixer reactor, said static-mixer reactor operatively connected to said extruder for receiving and bioreacting the starch substrate, said static-mixer reactor operatively configured to receive and add an alpha-amylase enzyme to the starch substrate; and
  (g) means for heating the starch substrate exiting said static-mixer reactor wherein the starch substrate is heated at a predetermined temperature for a predetermined duration such that inclusions remaining in the substrate are sufficiently digested.

28. The system according to claim 27 in which said extruder has a twin screw.

* * * * *